(12) United States Patent
Zeng et al.

(10) Patent No.: US 7,225,027 B2
(45) Date of Patent: May 29, 2007

(54) COCHLEAR IMPLANTS AND APPARATUS/METHODS FOR IMPROVING AUDIO SIGNALS BY USE OF FREQUENCY-AMPLITUDE-MODULATION-ENCODING (FAME) STRATEGIES

(75) Inventors: Fan-Gang Zeng, Irvine, CA (US); Kai-Bao Nie, Irvine, CA (US)

(73) Assignee: Regents of the University of California, Oakland, CA (US)

( * ) Notice: Subject to any disclaimer, the term of this patent is extended or adjusted under 35 U.S.C. 154(b) by 580 days.

(21) Appl. No.: 10/229,397

(22) Filed: Aug. 27, 2002

(65) Prior Publication Data

US 2003/0044034 A1 Mar. 6, 2003

Related U.S. Application Data

(60) Provisional application No. 60/315,278, filed on Aug. 27, 2001.

(51) Int. Cl.
*A61N 1/36* (2006.01)
(52) U.S. Cl. .................... 607/57; 607/137
(58) Field of Classification Search ............ 607/55–57
See application file for complete search history.

(56) References Cited

U.S. PATENT DOCUMENTS

| | | | |
|---|---|---|---|
| 3,360,610 A | 12/1967 | Flanagan | |
| 5,528,696 A | 6/1996 | Ribic | |
| 5,615,302 A | 3/1997 | McEachern | |
| 5,800,475 A | * | 9/1998 | Jules .................. 607/57 |
| 5,983,139 A | 11/1999 | Zierhofer | |
| 6,201,993 B1 | 3/2001 | Kruse et al. | |

OTHER PUBLICATIONS

Chen, H.B. et al., *Frequency modulation detection in cochlear implant subjects*, The Journal of Acoustical Society of America, vol. 116, No. 4, 2004, pp. 2269-2277.
Flanagan, J.L., *Phase Voceder*, Bell System Technology, 1966.
Nie, K. et al., *Independent Contributions of Amplitude and Frequency Modulations to Auditory Perception. I. Consonant, Vowel, and Sentence Recognition*, Abstracts of the 26th ARO Midwinter Research Meeting, P.A. Santi (Ed.), Daytona Beach, Florida, 2003, p. 214.
Kong, Y. et al., *Independent Contributions of Amplitude and Frequency Modulations to Auditory Perception, II. Melody, Tone, and Speaker Identification*, Abstracts of the 26th ARO Midwinter Research Meeting, P.A. Santi (Ed.), Daytona Beach, Florida, 2003, pp. 214-215.
Smith, Z. et al., *Chimaeric sounds reveal dichotomies in auditory perception*, Nature, vol. 416, No. 6876, Mar. 7, 2002, pp. 87-90.

* cited by examiner

*Primary Examiner*—George Manuel
*Assistant Examiner*—Nicole Kramer
(74) *Attorney, Agent, or Firm*—Crowell & Moring

(57) ABSTRACT

A method of improving sound quality of audio signals that are digitally processed includes steps of extracting amplitude and frequency modulations from one or more narrow bands of the audio signal, and filtering and compressing those modulations to produce amplitude and frequency modulated audio signals that are digitally processed to provide an acoustic signal similar to the original audio signal. The methods may be used in auditory prostheses and telecommunication systems.

19 Claims, 6 Drawing Sheets

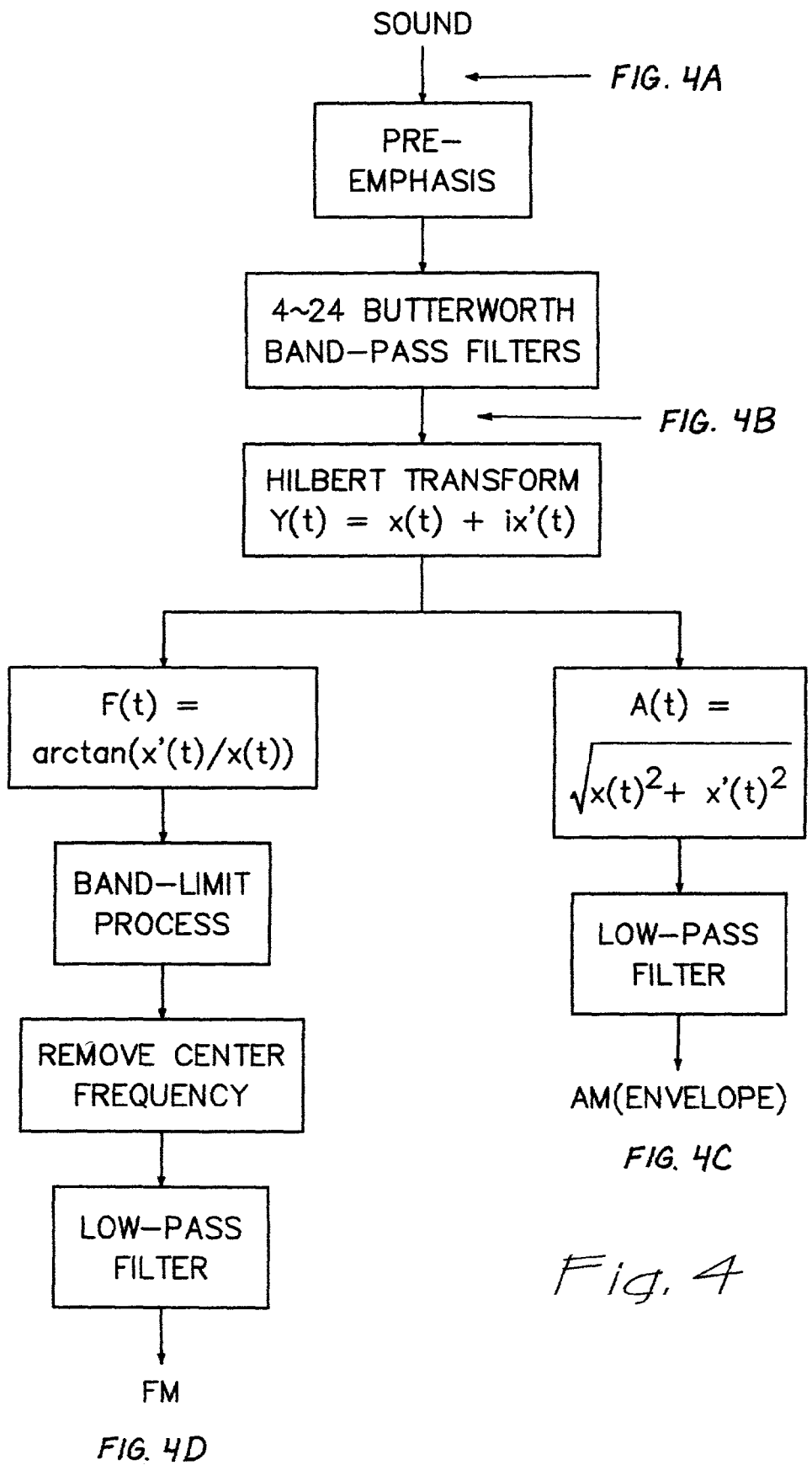

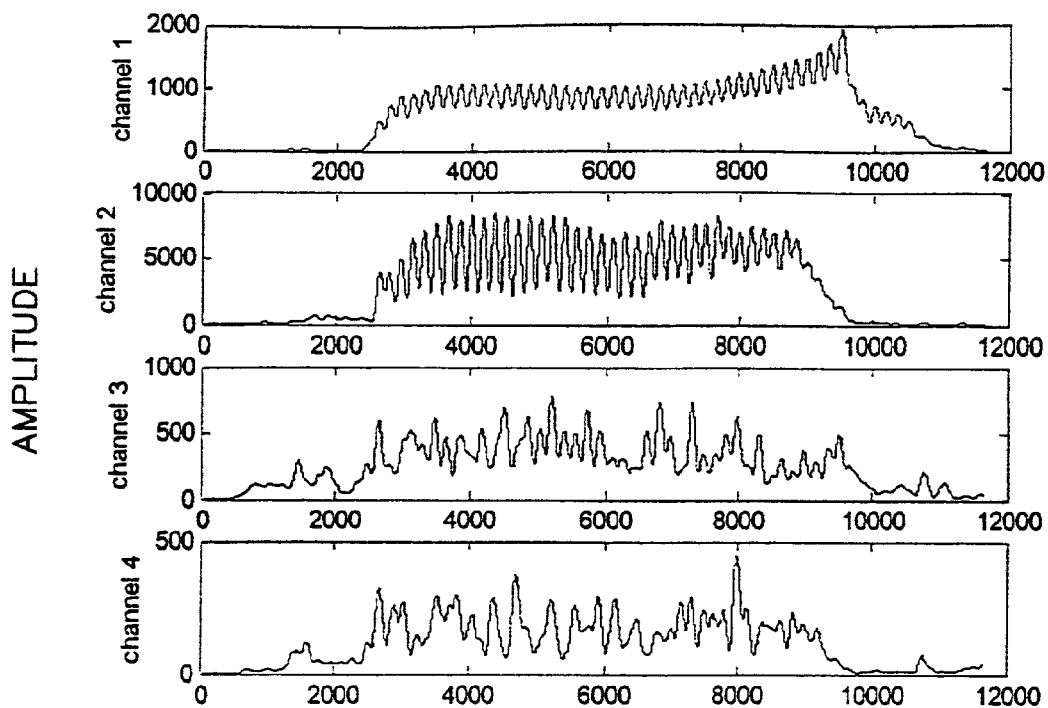
Fig. 4C
Fig. 4D
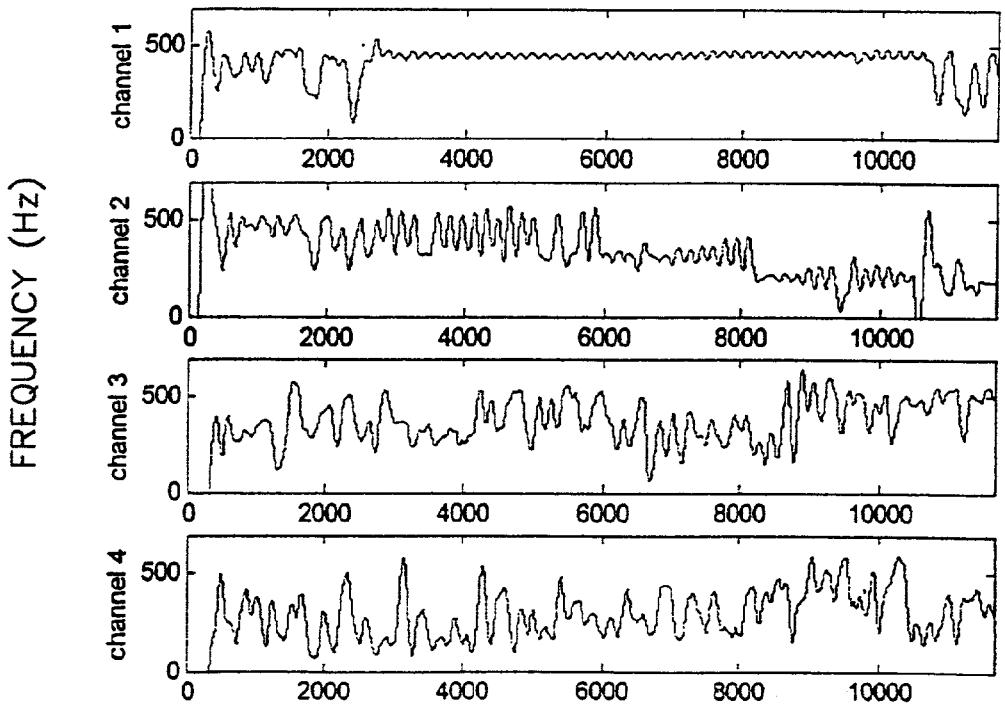

COCHLEAR IMPLANTS AND APPARATUS/METHODS FOR IMPROVING AUDIO SIGNALS BY USE OF FREQUENCY-AMPLITUDE-MODULATION-ENCODING (FAME) STRATEGIES

CROSS-REFERENCE TO RELATED APPLICATIONS

This application claims the benefit of U.S. Provisional Application No. 60/315,278, filed Aug. 27, 2001, the entire contents of which are hereby incorporated by reference.

STATEMENT REGARDING FEDERALLY SPONSORED RESEARCH

This invention was made with Government support under Grant RO1-DC02267-07 awarded by the National Institutes of Health. The Government may have certain rights in this invention.

FIELD OF THE INVENTION

The present invention relates to apparatus and methods for modifying acoustic signals, and more particularly, the invention relates to apparatus and methods that extract changes in amplitude and changes in frequency from acoustic signals, and use those extracted changes to provide high quality audio signals, which can be used in auditory prostheses and telecommunication devices.

BACKGROUND

All sounds are characterized by changes in amplitude and frequency. The auditory systems of humans and many mammals are sensitive to changes in amplitude and frequency. In the cochlear implants that have heretofore been available, only amplitude changes are extracted and encoded.

The cochlear implants of the prior art have generally employed two types of sound encoding strategies. In one type, only amplitude modulations are extracted and modulate a fixed rate carrier. see, Wilson et al., *Better Speech Recognition With Cochlear Implants*, Nature. 1991 July 18;352(6332):236-8. In the other type, filtered raw analog waveforms (including amplitude, frequency modulations and many other components) are delivered directly to electrodes to stimulate the neurons. see, Eddington et al., *Auditory Prostheses Research With Multiple Channel Intracochlear Stimulation In Man*, Ann Otol Rhinol Laryngol, 1978, 87 (6 Pt 2), 1-39.

Others have attempted to encode fundamental frequency (Fo) in cochlear implants. see, Geurts L, Wouters J., *Coding Of The Fundamental Frequency In Continuous Interleaved Sampling processors for cochlear implants*, J Acoust Soc Am. 2001 February;109(2):713-26; Faulkner A, Rosen S, Smith C., *Effects Of The Salience Of Pitch And Periodicity Information On The Intelligibility Of Four-Channel Vocoded Speech: Implications For Cochlear Implants*, J Acoust Soc Am. 2000 October; 108(4):1877-87.

In audio compression, there has been some recent research using amplitude and frequency modulations to encode speech. see, Potaminanos, A and Maragos P., *Speech Analysis And Synthesis Using An AM-FM Modulation Model*, Speech Communication, 1999:28, 195-209 Their studies are generally used to extract and trace frequency modulations at or near the format frequency, which varies by itself and has to be encoded during transmission. The present strategy will extract and code only frequency modulations at a fixed center frequency of a narrow band, which is known a priori in both the coder and the decoder, and needs not to be transmitted.

In cochlear implants, either amplitude modulation (only) or the analog waveform is encoded. One of them provides too little (AM only) while the other provides too much indiscriminable information. In audio coding, the encoding strategy has traditionally been considered from the speech production perspective and little perceptual information except for masking is used.

Although there exists a substantial body of knowledge relating to frequency modulation in basic auditory research, there has been little or no work done to encode frequency modulation in cochlear implants (or any other neural prosthetic devices) and use it in audio compression.

SUMMARY OF THE INVENTION

The present invention uses Frequency-Amplitude-Modulation-Encoding (FAME) to improve the quality of sound perception for the cochlear implant users and to compress audio signals so that broad-band qualities can be achieved with narrow-band transmission channels.

The FAME strategy extracts essential information (changes in amplitude and frequency) and is able to use a narrow-band capacity to provide broad-band (i.e. high-quality) audio signals, which can be used in auditory prostheses and telecommunication.

In cochlear implants, broad-band audio signals are first divided into narrow bands. Frequency and amplitude modulations are independently extracted from each band, and then processed with filtering and compression to produce frequency and amplitude modulated signals that are adequate for the perceptual capability in implant users or the bandwidth limitation of the transmission channels. The band-specific frequency and amplitude modulations may be used to directly stimulate the electrodes implanted in a person's head or re-synthesized to recover the original audio signals.

In audio coding, it is very challenging to encode a 10,000-10,300 Hz signal, but it would be much easier to encode the change (300 Hz) centered at that frequency. Since amplitude and frequency changes are independent and contain time information, the FAME strategy essentially transforms a 3-dimensional (amplitude, frequency, and time) encoding problem into a 2-dimensional problem.

The difference between these fundamental frequency encoding strategies and the present FAME strategy is that only fundamental frequency is used to modulate the carrier across some or all bands in the fundamental frequency encoding strategies, while in the applications of FAME strategy in accordance with this invention, the band-specific frequency modulations (which may or may not carry fundamental frequency information) will be extracted and used to modulate the carrier frequency in the corresponding band.

Frequency-Amplitude-Modulation-Encoding (FAME) strategy is aimed at improving perception of music, tonal-language speech, and speech in multiple-talker backgrounds ("cocktail party effect"). The same strategy can also be used to compress audio signals for all communication purposes including wired, or wireless and internet signal transmission, storage and retrieval of audio information.

BRIEF DESCRIPTION OF THE FIGURES

FIG. 4 is a flow diagram of a method for processing sound according to the present invention, incorporating a novel algorithm of the present invention.

FIG. 4C is a 4 channel graphic (Amplitude vs. Time) of the AM envelope obtained in the method of FIG. 4.

FIG. 4D is a 4 channel graphic (Frequency vs. Time) of the FM signal that results from application of the FAME algorithm and processing steps of the present invention as shown in FIG. 4.

DETAILED DESCRIPTION OF PRESENTLY PREFERRED EMBODIMENTS

Figure 1:
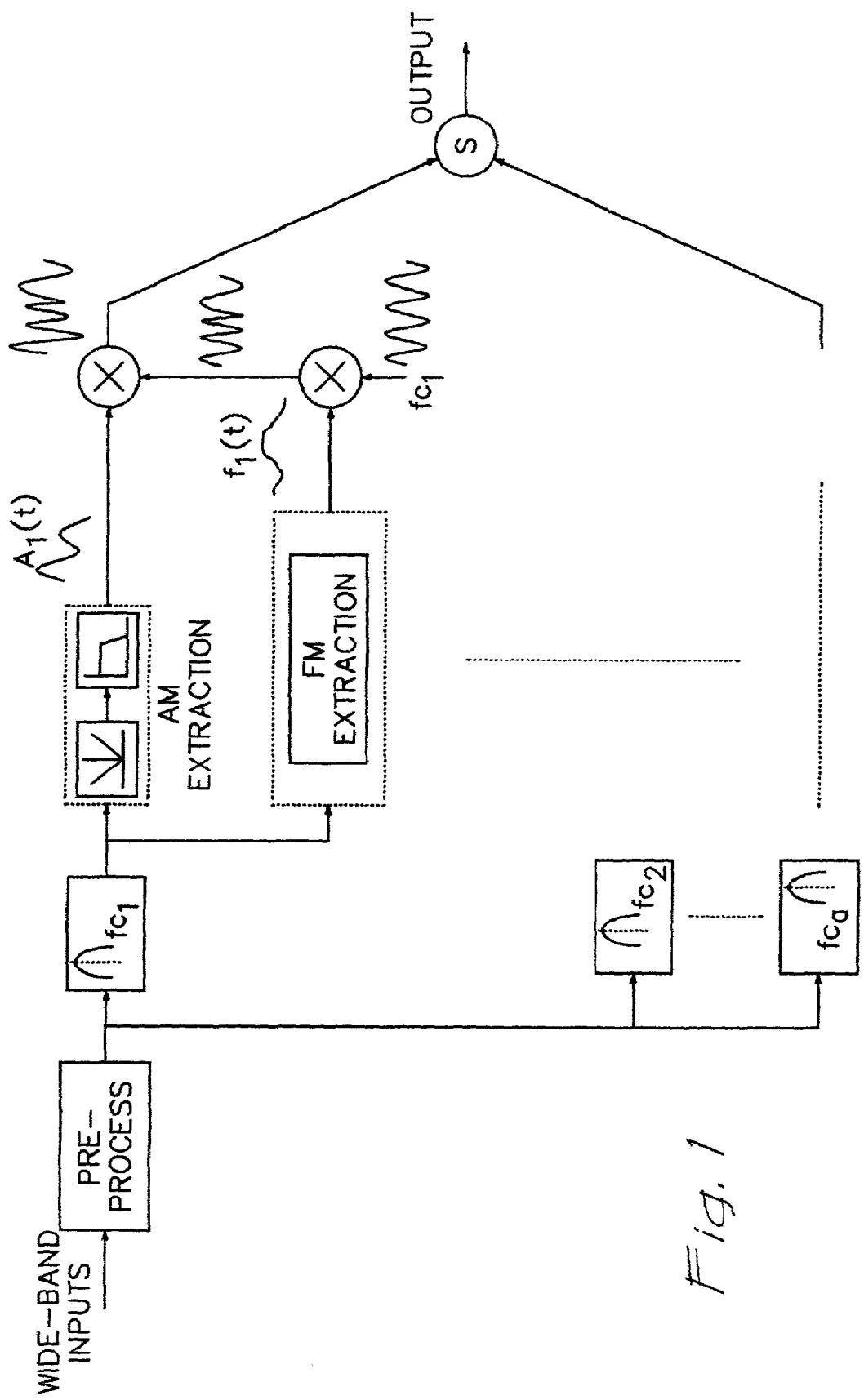
FIG. 1 is a flow diagram representing an acoustic simulation of the FAME strategy.

FIG. 1 shows an acoustic simulation of the FAME strategy. A wide-band signal (speech, music or any other audio signals) is first processed to have an ideal bandwidth and spectral shapes, e.g., 20-20000 Hz and spectral flattening for speech sound. The pre-processed audio signal is then filtered into N number of narrow frequency bands. N will be determined based on optimal recognition and compression. The narrow-band signal (only band 1 is demonstrated as an example) will be subject to parallel extraction of amplitude and frequency modulations. Amplitude modulation can be extracted by simple rectification and low-pass filtering as shown in the diagram, or digital Hilbert transfer. Frequency modulation can be extracted by calculating the instantaneous phase angle (frequency) of the fine-structure or zero-crossings of the narrow-band signal. The FM can have a wide range of instantaneous frequency, which will be filtered and/or compressed based on the perceptual evaluations in both normal-hearing and cochlear-implant listeners. In the present implementation, only the 300-Hz FM range is used to modulate a sinusoidal frequency equal to the center frequency of the analysis bandpass filter (fcl). Note that FM changes the frequency of this carrier but not the amplitude of the resulting waveform. The extracted temporal envelope [A1(t)] is then amplitude-modulated to the FM carrier, resulting in a band-specific frequency-amplitude-modulated waveform. These waveforms from all N bands will be summed to produce an acoustic simulation of the FAME strategy.

Figure 2:
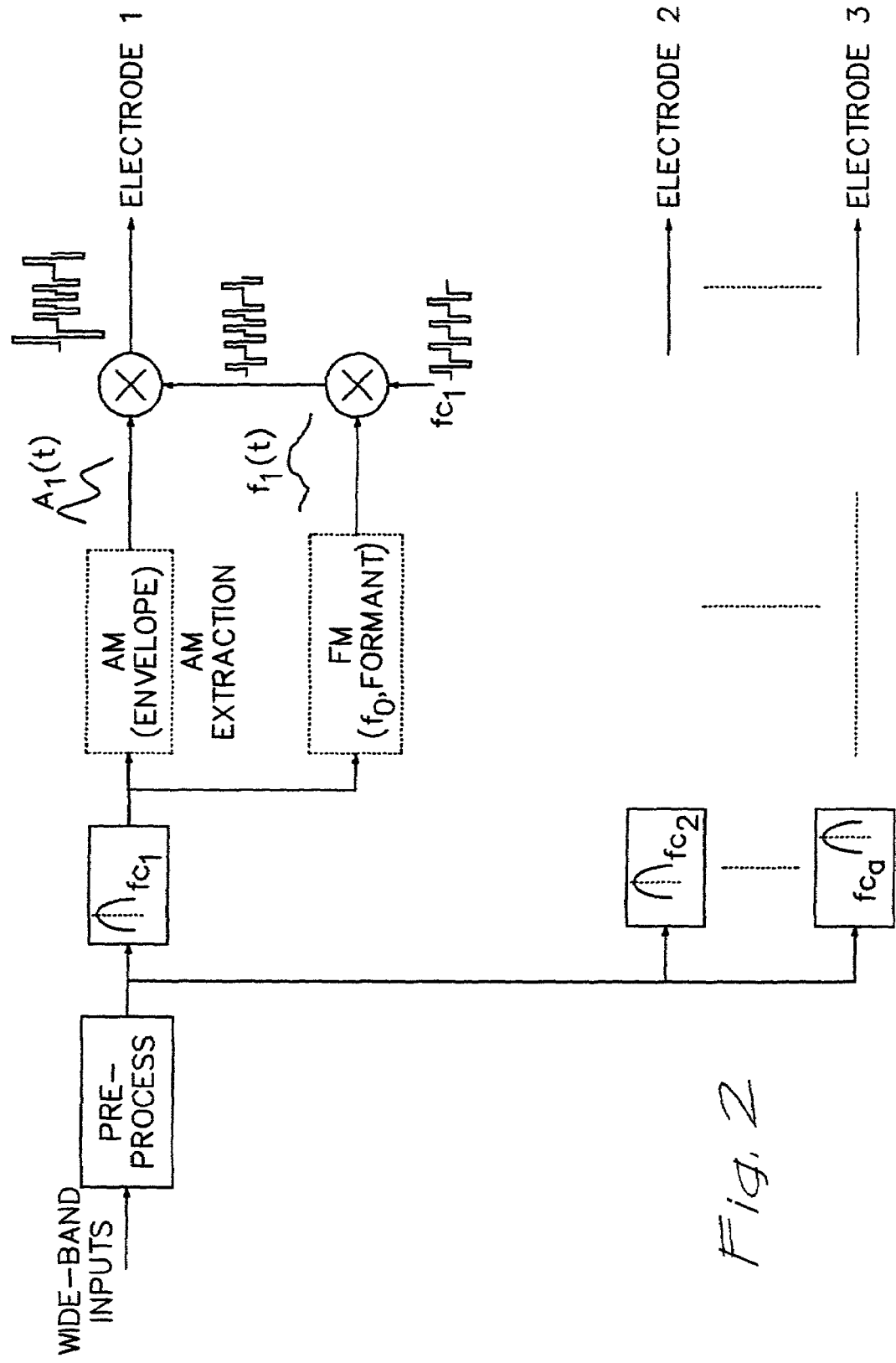
FIG. 2 is a flow diagram sowing a method for implementation of the FAME strategy in a cochlear implant.

FIG. 2 shows implementation of the FAME strategy in a cochlear implant. All initial processing steps are the same as in the acoustic simulation (FIG. 1) except that in this example, the carrier comprises biphasic pulses. These pulses are first frequency modulated so that inter pulse interval varies according to the frequency modulation (slow-fast-slow) pattern. The FM pulse train will then be amplitude modulated as in the case of the present cochlear implants. Because the perceived place pitch is dominantly coded by the electrode position in the cochlea, the center frequency of the carrier can be either the center frequency of the narrow-band (fcn) or a fixed-rate (e.g., 1000 Hz) pulse train. Alternatively, only FM will be amplitude-modulated to produce final frequency-amplitude-modulated pulses. To avoid the pulse overlap between electrodes, the exact position of the pulses will be varied to result in non-simultaneous stimulation across electrodes. An algorithm will be developed to minimize the change in FM due to the small changes in pulse position within each electrode channel as well as across all channels. An example of one such algorithm is shown in the flow diagram of FIG. 4.

Figure 3:
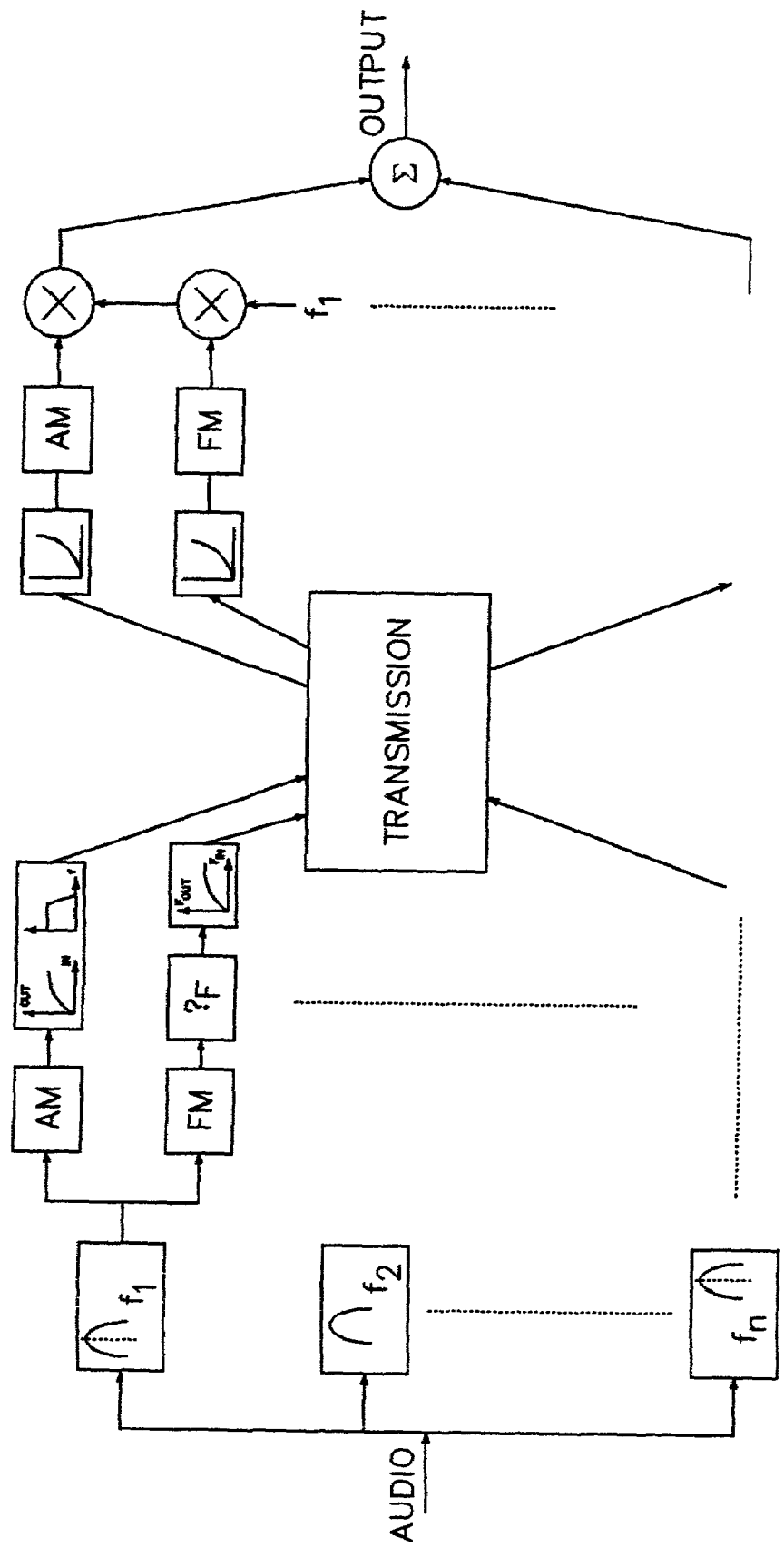
FIG. 3 is a flow diagram showing a method for using FAME to encode general audio signals.

FIG. 3 shows that FAME can be used to encode general audio signals. Band-specific FM and AM will be extracted and compressed for encoded transmission over wired or wireless channels. Because the center frequencies are known on both coding and decoding sides, they need not to be transmitted. The transmitted FM and AM will be restored and synthesized to recover the original audio signal. For each channel, the AM would require 200 bits/sec (8 bits×25 Hz) and the FM would require 300 bits/sec (1 bit zero-crossing×300 Hz), resulting in a total of 500 bits/sec. Because 8-10 channels are likely sufficient to provide high-quality audio signals, a total of 4.8 kbits/sec can be used in a wide range of communication channels.

Cochlear implants and audio compression systems of the present invention (i.e., using the FAME strategy) provide a substantial improvement over the prior art strategy of only coding amplitude modulations. The strategy of coding amplitude modulations, while providing good speech recognition in noise, is not adequate to cope with speech in noise, music perception, and tonal language perception. On the other hand, the analog waveforms theoretically contain all amplitude and frequency modulations, but information regarding these modulations is not accessible to implant users in an unprocessed fashion. Thus, the application of FAME strategies to cochlear implants and audio signals is a significant and inventive improvement.

Figure 4A:
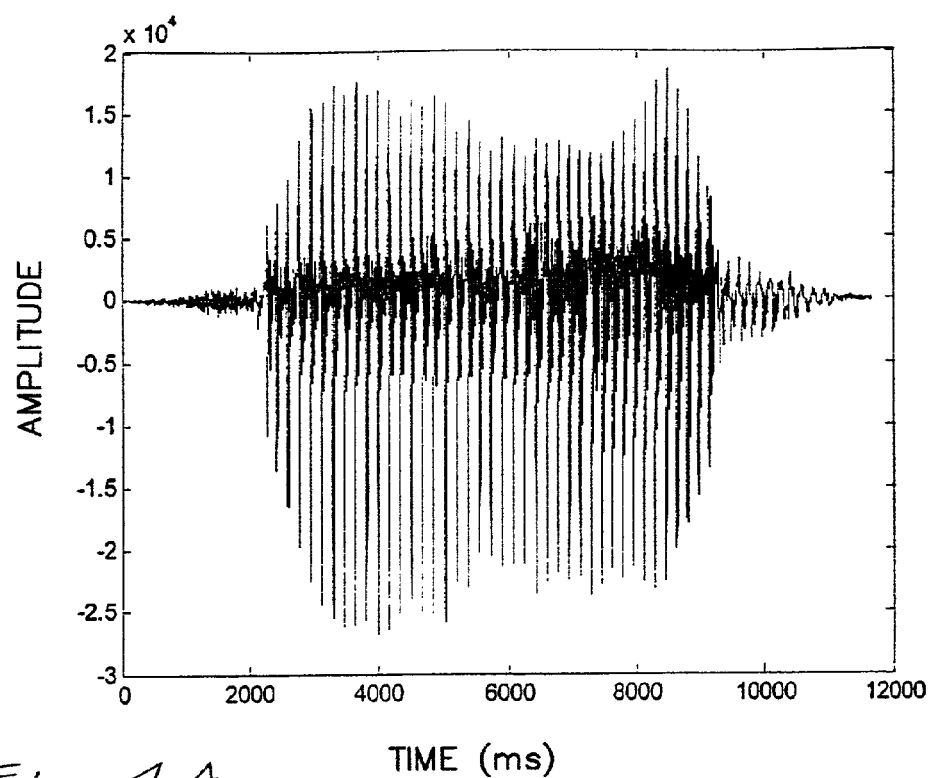
FIG. 4A is a graph (Amplitude vs. Time) of the original sound of FIG. 4.
Figure 4B:
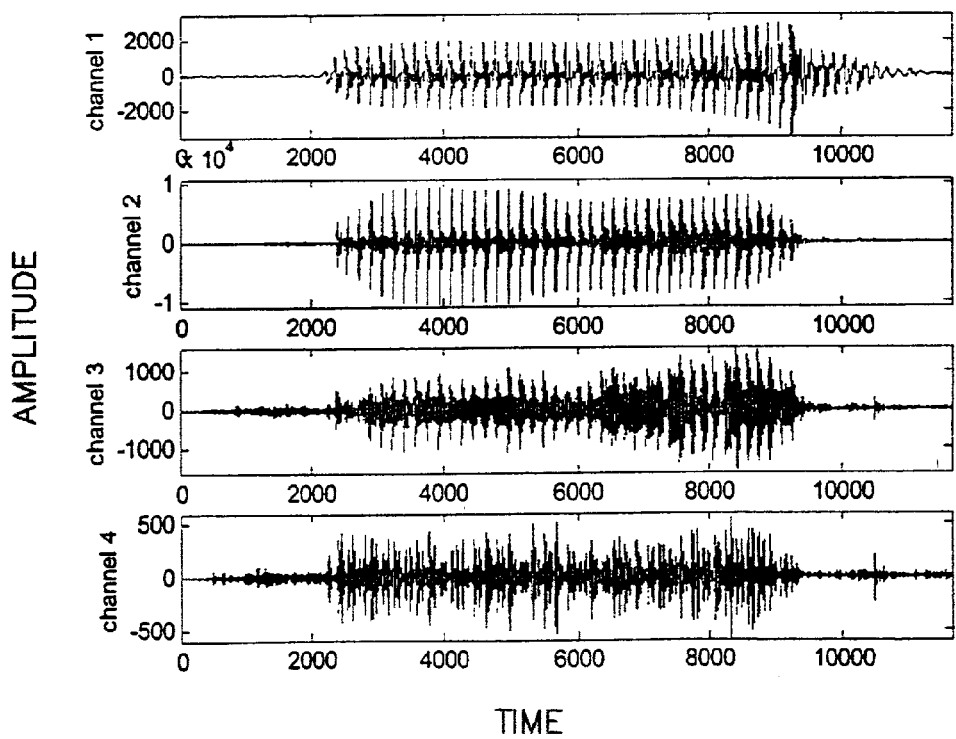
FIG. 4B is a 4 channel graphic (Amplitude vs. Time) of the sound of FIG. 4 after the "pre-emphasis" and "4~24 Butterworth Band Pass Filter steps have been performed.

FIGS. 4-4D show an example of a method of the present invention, wherein a sound (FIG. 4A) is processed to provide an AM (envelope) signal (FIG. 4C) and an FM signal (FIG. 4D) that is obtained by application of FAME strategy using a FAME algorithm in accordance with the present invention.

We claim:

1. A cochlear implant, comprising:
   at least one electrode structured to be placed in a patient's cochlea; and
   an acoustic signal encoder in communication with the at least one electrode and effective to stimulate the at least one electrode, the acoustic signal encoder comprising:
   (a) an amplitude modulation extractor effective to extract amplitude modulations from at least one band of an acoustic signal,
   (b) a frequency modulation extractor effective to extract frequency modulations from the at least one band of the acoustic signal, and
   (c) a signal processor effective to compress the amplitude and frequency modulations to produce amplitude and frequency modulated electric signals that are used to stimulate the at least one electrode of the cochlear implant.

2. The cochlear implant of claim 1, comprising a frequency modulator that modulates frequency of an acoustic signal so that an inter-pulse interval of the acoustic signal varies according to a frequency modulation pattern.

3. The cochlear implant of claim 1, comprising an amplitude modulator.

4. The cochlear implant of claim 1, comprising a plurality of electrodes.

5. The coohlear implant of claim 4, comprising a pulse controller that controls positioning of frequency-amplitude-modulated pulses generated by the signal encoder to reduce simultaneous stimulation across the plurality of electrodes.

6. The cochlsar implant of claim 1 wherein the amplitude modulation extractor comprises a transformer.

7. The cochlear implant of claim 6 wherein the transformer is a Hilbert transformer.

8. The cochlear implant of claim 1 wherein the amplitude modulation extractor comprises a rectifier.

9. The cochlear implant of claim 1 wherein the amplitude modulation extractor comprises a low pass filter.

10. The cochlear implant of claim 1 wherein the amplitude modulation extractor comprises a rectifier/low pass filter.

11. The cochlear implant of claim 1 wherein the amplitude modulation extractor comprises a transformer and a rectifier/low pass filter.

12. The cochlear implant of claim 1 wherein the frequency modulation extractor comprises a band pass filter.

13. The cochlear implant of claim 1 wherein the signal processor is further effecUve to filter the amplitude and frequency modulations extracted from the at least one band.

14. The cochlear implant of claim 1 further comprising a pre-processor in communication with the signal encoder, the pre-processor being effective to divide a broad band acoustic signal into a plurality of narrow band signals that are passed to the signal encoder.

15. The cochlear implant of claim 14 which is effective to produce a band-specific frequency-amplitude modulated waveform that simulates the broad band acoustic signal provided to the pre-processor.

16. The cochlear implant of claim 1 wherein the at least one band comprises a plurality of bands and the signal encoder is effective to extract amplitude and frequency modulations from the bands on an individual basis.

17. The cochlear implant of 1 wherein the frequency modulation extractor is effective to calculate an instantaneous phase angle of the at least one band of the acoustic signal at a region of where the amplitude of the acoustic signal is approximately zero.

18. The cochlear implant of claim 1 wherein the amplitude modulation extractor is effective to extract a temporal envelope from the at least one band of the acoustic signal.

19. The cochlear implant of claim 18 wherein the signal processor is effective to modulate the amplitude of the extracted temporal envelope.

* * * * *